(12) United States Patent
Michael

(10) Patent No.: US 9,381,119 B2
(45) Date of Patent: *Jul. 5, 2016

(54) METHODS AND APPARATUS FOR CONTINUOUS NOISE EXPOSURE MONITORING

(75) Inventor: Kevin Michael, Furnace, PA (US)

(73) Assignee: Honeywell International Inc., Morris Plains, NJ (US)

(*) Notice: Subject to any disclaimer, the term of this patent is extended or adjusted under 35 U.S.C. 154(b) by 401 days.

This patent is subject to a terminal disclaimer.

(21) Appl. No.: 12/880,967

(22) Filed: Sep. 13, 2010

(65) Prior Publication Data

US 2011/0058680 A1  Mar. 10, 2011

Related U.S. Application Data

(63) Continuation of application No. 11/130,267, filed on May 17, 2005, now Pat. No. 7,978,861.

(60) Provisional application No. 60/571,511, filed on May 17, 2004.

(51) Int. Cl.
*A61F 11/08* (2006.01)
*G01H 3/14* (2006.01)

(52) U.S. Cl.
CPC . *A61F 11/08* (2013.01); *G01H 3/14* (2013.01)

(58) Field of Classification Search
CPC .... H04R 25/65; H04R 25/656; H04R 1/1016; H04R 2225/023; H04R 2225/025; H04R 2460/01; H04R 2410/05; H04R 1/1075; A61F 11/08
USPC .............. 381/60, 72, 74, 312, 315, 317, 328
See application file for complete search history.

(56) References Cited

U.S. PATENT DOCUMENTS

| | | | |
|---|---|---|---|
| 3,578,104 A | 5/1971 | Sotome | |
| 3,697,973 A | 10/1972 | Stevens et al. | |
| 3,802,535 A | 4/1974 | Peake et al. | |
| 3,848,471 A | 11/1974 | Hamburg et al. | |
| 3,865,998 A * | 2/1975 | Weiss et al. | 381/324 |
| 3,968,334 A | 7/1976 | Padilla | |
| 4,020,298 A | 4/1977 | Epley et al. | |
| 4,060,701 A | 11/1977 | Epley | |

(Continued)

*Primary Examiner* — Duc Nguyen
*Assistant Examiner* — George Monikang
(74) *Attorney, Agent, or Firm* — Conley Rose, P.C.; Kristin Jordan Harkins

(57) ABSTRACT

A method for continuously monitoring noise exposure level of a person via measuring sound level within an ear canal of the person using a sound measurement means linked to a sound level recording device external to the ear canal, wherein the sound measurement means may be shielded from the environment by a hearing protective device, and wherein the cable does not interfere with the ability of the hearing protective device to reduce noise exposure level in the ear canal. Also provided is a system comprising a sound measurement means mounted within an ear canal of the person, an external sound level recording means and a linking cable. Further provided is a system for providing continuous noise exposure monitoring level of a person, and for providing radio communication in a noisy environment, said system comprising the above sound monitoring system linked to a radio signal transmission means, and is switchable between said sound level recording means in a recording mode and said radio signal transmission means in a communication mode.

19 Claims, 3 Drawing Sheets

(56) References Cited

U.S. PATENT DOCUMENTS

| | | |
|---|---|---|
| 4,307,385 A | 12/1981 | Evans et al. |
| 4,674,161 A | 6/1987 | Edinger et al. |
| 5,113,967 A | 5/1992 | Killion et al. |
| 5,317,273 A | 5/1994 | Hanson et al. |
| 5,426,719 A * | 6/1995 | Franks ............... H04R 1/46 381/72 |
| 5,631,965 A | 5/1997 | Chang et al. |
| 5,757,930 A | 5/1998 | Seidemann et al. |
| 5,917,923 A | 6/1999 | Caron et al. |
| 6,126,588 A * | 10/2000 | Flamant ............... A61L 15/18 600/15 |
| 6,456,199 B1 | 9/2002 | Michael |
| 7,006,647 B1 | 2/2006 | Wuersch |
| 7,313,245 B1 * | 12/2007 | Shennib ............... A61F 11/08 128/864 |
| 8,249,266 B2 | 8/2012 | Michael |
| 2001/0005421 A1 | 6/2001 | Harris |
| 2001/0050993 A1 | 12/2001 | Douglas |
| 2002/0080979 A1 | 6/2002 | Brimhall et al. |
| 2003/0019661 A1 * | 1/2003 | Aoyama ............... H01B 1/026 174/126.1 |
| 2005/0018859 A1 * | 1/2005 | Buchholz ............... 381/74 |
| 2005/0232453 A1 | 10/2005 | Fideler |

\* cited by examiner

METHODS AND APPARATUS FOR CONTINUOUS NOISE EXPOSURE MONITORING

CROSS REFERENCE FOR RELATED APPLICATIONS

This application is a continuation of and claims benefit under 35 USC §120 at the time of filing U.S. Pat. No. 7,978,861 entitled "Method and Apparatus for Continuous Noise Exposure Monitoring" issued Jul. 12, 2011, which in turn was related to and claims benefit under 35 USC §119 to U.S. Provisional Patent Application No. 60/571,511, filed May 17, 2004, all of which are claimed for priority, are assigned to the Assignee of the present application, and are hereby expressly incorporated by reference as if reproduced in their entirety.

BACKGROUND OF THE INVENTION

Long-term exposure to high levels of noise may cause hearing loss and other health hazards, and as a consequence U.S. law requires that the exposure level to noise by an individual in a work place be accurately measured and limited. See e.g. 29 C.F.R. §1910.95, and U.S. Pat. No. 6,456,199 for a general discussion. Noise dosimeter is commonly used in the industry to measure the cumulative noise exposure by an individual over the course of a full work shift, and the effectiveness of hearing protection devices (HPD) or noise control devices.

U.S. Pat. No. 6,456,199, incorporated herein by reference, discloses a cost-effective and unobtrusive means of continuously monitoring an individual's actual noise exposure rather than simply measuring either hearing protector attenuation or unprotected individual exposure.

The monitoring system includes at least one microphone, housed in the interior of a hearing protective device. Exposure dosage calculation includes periods when the HPD is worn (primary microphone position) and periods when it is not worn (secondary microphone position). When the HPD is worn at the primary position, it measures the noise level with the protective device in effect, and when the HPD is worn at the secondary position, it measures the noise level of the environment without the protective device. This provides an accurate measurement of the actual exposure dosage because invariably workers have their hearing protectors donned for part of the day and removed for the rest of the day.

Methods of measuring noise dose or sound level incident upon the worker's ear canal ("in-the-ear-canal sound level measurements") are known in the prior art, but are performed with a probe tube microphone. These devices are not suitable for measuring under hearing protectors. First, the tube breaks the seal of the protector, thus compromising the protection. Second, the tube is acoustically transparent at some frequencies, making the system inappropriate for use in high noise areas. For example, U.S. Pat. No. 5,757,930 to Seidemann, describes a system of noise measurement interior to an insert-type hearing protector. This system consists of a microphone mounted at the interior tip of a modified earplug, not mounted in the ear canal. The Seidemann system is designed to measure hearing protector attenuation, not personal noise exposure. Once the earplug is removed (unprotected condition), it no longer measures the noise exposure level in the ear canal. Furthermore, the Seidemann system is not usable with muff-type HPDs.

BRIEF DESCRIPTION OF THE DRAWINGS

For a more complete understanding of the present disclosure, and for further details and optional advantages thereof, reference is now made to the accompanying drawings, wherein.

DESCRIPTION OF THE INVENTION

The present invention discloses an alternative to the methodology of U.S. Pat. No. 6,456,199, and associated devices useful therefore. According to one embodiment of the present invention, a miniature microphone is mounted in the worker's ear canal for the entire duration of the work shift, and noise level incident to the ear canal is constantly measured. Using this technique, the measurement accurately reflects the actual noise exposure level at the worker's ears.

According to the present invention, the microphone stays in one position, accurately measuring exposure under both protected and unprotected conditions. An advantage of the present invention is that conventional hearing protection devices, such as ear muffs or ear plugs, can be used by the workers, without interfering with the accurate measurement of the actual exposure levels of the workers. In the unprotected condition (i.e., an HPD is not worn), the ear canal microphone accurately measures the sound pressure that is incident on the ear canal. In the protected condition, the canal-mounted microphone measures the sound pressure that is present interior to the hearing protection.

One key advantage of the present invention is that the measurement microphone stays constantly in one position within the worker's ear canal, thereby providing the most accurate measurement of "center-of-head" (COH) noise exposure, the definitive metric used by the United States Occupational Safety and Health Administration (OSHA) and Mining Safety and Health Administration (MSHA) to determine noise regulation compliance. Laboratory comparison measurements have verified that the "in-the-ear-canal" sound level or noise dose measurements of the present invention accurately reflect the COH equivalent. All damage risk criteria in the US have been developed using the COH with the worker absent as the default measurement location.

Another advantage of the present invention is that it is compatible with commercially available hearing protective devices and existing communication systems.

Figure 1:
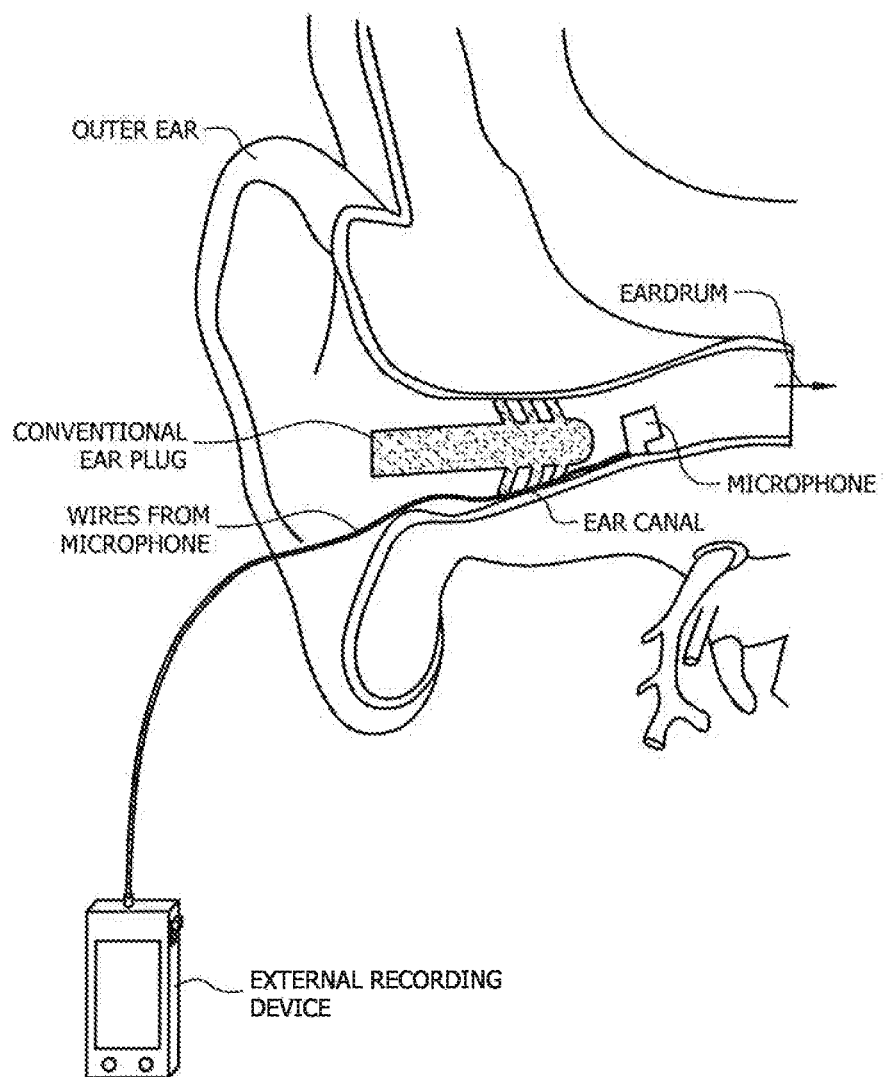
FIG. 1 is an exemplary schematic drawing illustrating an embodiment of the apparatus for continued noise monitoring in place within a user's ear canal, when used with an exemplary conventional earplug.
Figure 2:
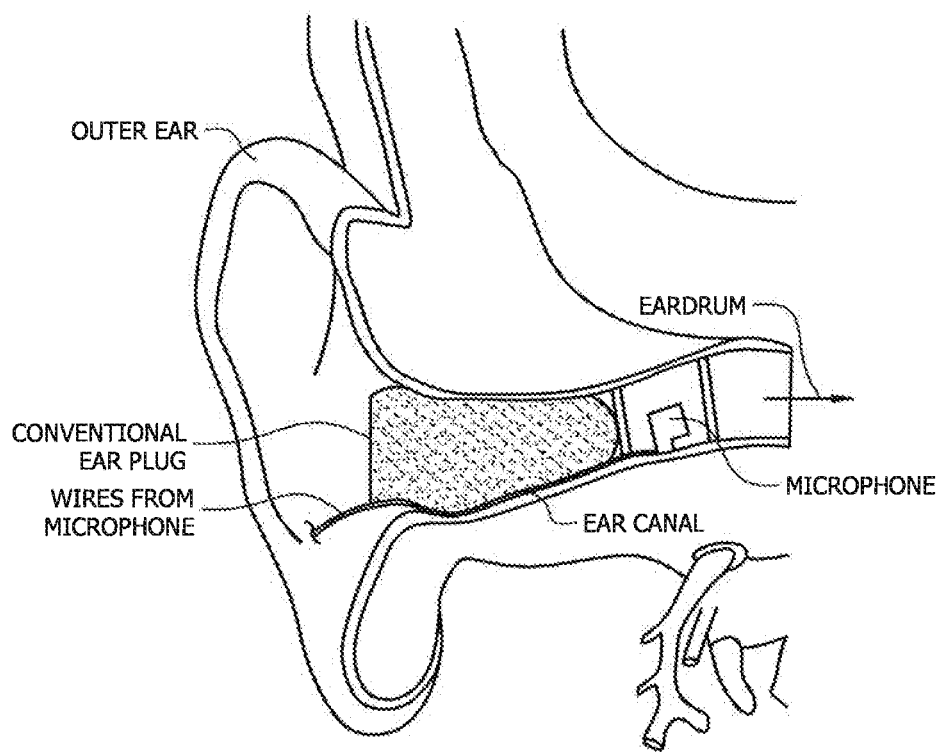
FIG. 2 is an exemplary schematic drawing illustrating another embodiment of the apparatus for continued noise monitoring in place within a user's ear canal, when used with an exemplary conventional earplug.

Microphones suitable for the present invention should be constructed or positioned in such a way that an insert-type earplug cannot be inserted over the microphone. Occlusion by the earplug inside the ear canal will render the measurements inaccurate (see FIG. 1). One approach to accomplish this objective is using a small, sound-transparent cage to enclose the microphone (see e.g. FIG. 2).

The measurement microphone is generally linked via cables or wires to an electrical signal modulating and/or recording device, to record and calculate the sound level.

According to the present invention, the wires or cables extending from the microphones to the external circuitry should not cause a breach of the sound barrier of the HPD.

Figure 3:
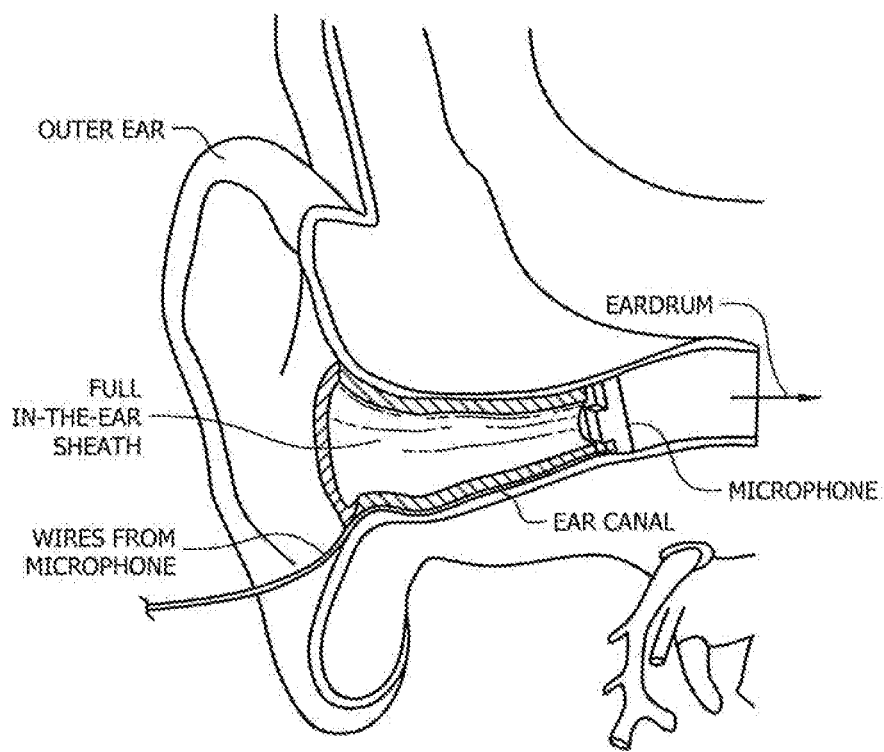
FIG. 3 is an exemplary schematic drawing illustrating another embodiment of the apparatus for continued noise monitoring in place within a user's ear canal, and having a sheath.

Thus, the cables or wires should be thin, e.g. preferably, 36 AWG or smaller, so that an effective seal can be made with the plug against the canal walls. Alternatively, the wires extending from the microphone to the external components can be embedded in a shell-like device that conforms to the ear canal walls, see for example FIG. 3.

This thin, shell-like device, or in-the-ear (ITE) sheath, is preferably constructed of a hypo-allergenic silicone material, and would be designed to accept insert-type hearing protectors. In preferred embodiments, the present invention provides a range of ITE sheath sizes to fit most ear canal sizes and geometries. The ITE sheath device may also be customized to fit a particular individual user's ears, if desired.

While this ITE device is designed to be flexible to conform to the ear canal walls, it is also stiff enough to remain open to ensure that sound can reach the measurement microphone.

One further advantage of the instant method is that it is well-suited for a combined hearing protection and 2-way radio communication system. The radio communication transceiver(s) can be mounted adjacent to the monitoring microphone. The communication speaker introduces an audible signal near the eardrum.

The communication microphone would also be able to pick up and transmit audio signals that are introduced into the ear canal when the worker speaks, but not environmental noise. This is a particularly effective communication system in noisy environments.

I claim:

1. A system for continuously monitoring noise exposure level of a person, said system comprising:
    a sound measurement means for measuring sound level, a sound level recording means, and a cable linking the sound measurement means and the sound level recording means;
    wherein the sound measurement means is configured to be mounted within an ear canal of the person; wherein the sound level recording means is configured to be external to the ear canal; wherein the sound measurement means is configured to be shielded from noise from an external environment by an insert-type hearing protective device that is separate and apart from the sound measurement means; wherein the cable is configured to not interfere with the ability of the insert-type hearing protective device to reduce the noise exposure level in the ear canal; and wherein the sound measurement means is not mounted on the insert-type hearing protective device, but is configured to be mounted within the ear canal independently of the insert-type hearing protective device; wherein the sound measurement means measures center-of-head noise exposure under both protected and unprotected conditions while located in only a single position within the ear canal of the person.

2. A system according to claim 1, said system further comprising a single hearing protective device, wherein the hearing protective device is separate from the sound measurement means and is not attached to the sound measurement means, such that the sound measurement means operates to measure the sound level within the ear canal of the person both when the hearing protective device is in place to shield the ear canal and when the hearing protective device is not in place.

3. A system according to claim 1, wherein the sound measurement means is a microphone.

4. A system according to claim 1, wherein the hearing protective device is a conventional ear plug.

5. A system according to claim 1, wherein the sound measurement means is enclosed in a sound-transparent cage in the ear canal between the hearing protective device and an eardrum.

6. A system according to claim 5, wherein the sound-transparent cage prevents the insert-type hearing protective device from being inserted over the sound measurement means.

7. A system according to claim 1, wherein the cable is embedded in a shell which fits snuggly and independently in the ear canal separate and apart from the hearing protective device, wherein the shell conforms to ear canal walls.

8. A system according to claim 7, wherein the shell allows for insertion of the insert-type hearing protective device within the shell.

9. A system according to claim 7, wherein the shell comprises a thin walled in-the-ear sheath with an opening, an exterior surface that conforms to the ear canal walls, and an interior surface of the opening that removeably accepts the separate insert-type hearing protective device for optionally sealing the opening and shielding the sound measurement means from the external noise environment;
    wherein the sound measurement means is attached to the shell so as to be operable to be shielded from the external noise environment when the insert-type hearing protective device is in place sealing the opening; and
    wherein the sound measurement means is operable to measure center-of-head noise exposure under both protected and unprotected conditions while located in only the single position within the ear canal of the person.

10. A system according to claim 9, wherein the shell is made of a hypo-allergenic silicon material.

11. A system according to claim 1, wherein the cable is located external to the hearing protective device and is 36 AWG or smaller so that the cable will not interfere with the hearing protective device's ability to form an effective seal within the ear canal, despite the cable being located between the hearing protective device and a wall of the ear canal.

12. A system for continuously monitoring noise exposure level of a person, said system comprising:
    a sound measurement means for measuring sound level, a sound level recording means, and a means for linking the sound measurement means and the sound level recording means so that sound level measurements are transmitted to the sound level recording means;
    wherein the sound measurement means is mounted within an ear canal of the person; wherein the sound level recording means is external to the ear canal; wherein the sound measurement means is optionally shielded from the noise environment by an insert-type hearing protective device that is separate and distinct from the sound measurement means; wherein the means for linking the sound measurement means and the sound level recording means does not interfere with the ability of the hearing protective device to reduce the noise exposure level in the ear canal; and wherein the sound measurement means measures exposure under both protected and unprotected conditions while located in only a single position.

13. A system according to claim 12, wherein the means for linking the sound measurement means and the sound level recording means comprises a cable; and wherein the cable is located external to the hearing protective device and is 36 AWG or smaller so that the cable will not interfere with the hearing protective device's ability to limn an effective seal within the ear canal, despite the cable being located between the hearing protective device and a wall of the ear canal.

14. A system according to claim 12, wherein the sound measurement means is enclosed in a sound-transparent cage in the ear canal between the hearing protective device and an eardrum.

15. A system according to claim 14, wherein the sound-transparent cage prevents the insert-type hearing protective device from being inserted over the sound measurement means.

16. A system according to claim 12, wherein the means for linking the sound measurement means and the sound level recording means comprises a cable; wherein the cable is embedded in a shell which fits snuggly in the ear canal; and wherein the shell comprises a thin in-the-ear sheath with an opening, an exterior surface that conforms to ear canal walls, and an interior surface of the opening that accepts the insert-type hearing protective device for optionally sealing the opening and shielding the sound measurement means from the environment.

17. A system for continuously monitoring noise exposure level of a person, said system comprising:
 a sound measurement means for measuring sound level, a sound level recording means, and a means for linking the sound measurement means and the sound level recording means;
 wherein the sound measurement means is configured to be mounted within an ear canal of the person; wherein the sound measurement means is configured to be optionally shielded from noise from an external environment by an insert-type hearing protective device that is separate and apart from the sound measurement means; wherein the insert-type hearing protective device is operable to reduce the noise exposure level when in place in the ear canal; wherein the sound level recording means is configured to be external to the ear canal; wherein the means for linking the sound measurement means and the sound level recording means is operable to not substantially interfere with the ability of the hearing protective device to reduce the noise exposure level in the ear canal; and wherein the sound measurement means is configured to measure noise exposure under both protected and unprotected conditions while located in only a single position within the ear canal of the person.

18. A system according to claim 17, said system further comprising the insert-type hearing protective device; wherein the insert-type hearing protective device is separate and independent from the sound measurement means, such that the sound measurement means operates to measure sound level within the ear canal of the person both when the insert-type hearing protective device is in place to shield the ear canal and when the insert-type hearing protective device is not in place; wherein the sound measurement means is operable to be mounted in the ear canal independently of the insert-type hearing protective device; wherein the sound measurement means is enclosed in a sound-transparent cage in the ear canal between the insert-type hearing protective device and an eardrum; and wherein the sound-transparent cage is operable to prevent the insert-type hearing protective device from being inserted over the sound measurement means.

19. A system according to claim 17, wherein the means for linking the sound measurement means and the sound level recording means comprises a cable; wherein the cable is embedded in a thin shell which fits snuggly in the ear canal; and wherein the shell comprises an in-the-ear sheath with an outward-facing opening configured to accept the insert-type hearing protective device, an exterior surface that conforms to ear canal walls, and an interior surface of the opening that accepts the insert-type hearing protective device for optionally sealing the opening and shielding the sound measurement means from the external noise environment.

\* \* \* \* \*